United States Patent
Lee et al.

(10) Patent No.: US 10,351,592 B2
(45) Date of Patent: Jul. 16, 2019

(54) METHOD FOR SEPARATING ANTIBODY ISOFORMS USING CATION EXCHANGE CHROMATOGRAPHY

(71) Applicant: CELLTRION, INC., Incheon (KR)

(72) Inventors: Dong Woo Lee, Incheon (KR); Mi Na Song, Incheon (KR); Byoung Oh Kwon, Incheon (KR); Ki Sung Kwon, Seoul (KR); Dong Rim Yeom, Incheon (KR); Yeon Jung Kim, Incheon (KR)

(73) Assignee: CELLTRION, INC., Incheon (KR)

( * ) Notice: Subject to any disclaimer, the term of this patent is extended or adjusted under 35 U.S.C. 154(b) by 360 days.

(21) Appl. No.: 15/033,335

(22) PCT Filed: Oct. 24, 2014

(86) PCT No.: PCT/KR2014/010088
§ 371 (c)(1),
(2) Date: Apr. 29, 2016

(87) PCT Pub. No.: WO2015/064971
PCT Pub. Date: May 7, 2015

(65) Prior Publication Data
US 2016/0264618 A1 Sep. 15, 2016

(30) Foreign Application Priority Data

Oct. 30, 2013 (KR) .................. 10-2013-0129688

(51) Int. Cl.
| | | |
|---|---|---|
| *C07K 1/18* | (2006.01) | |
| *C07K 1/22* | (2006.01) | |
| *C07K 1/36* | (2006.01) | |
| *C07K 16/06* | (2006.01) | |
| *C07K 16/28* | (2006.01) | |

(52) U.S. Cl.
CPC .................. *C07K 1/18* (2013.01); *C07K 1/22* (2013.01); *C07K 1/36* (2013.01); *C07K 16/065* (2013.01); *C07K 16/2863* (2013.01); *C07K 16/2887* (2013.01)

(58) Field of Classification Search
None
See application file for complete search history.

(56) References Cited

U.S. PATENT DOCUMENTS

| | | | | |
|---|---|---|---|---|
| 6,339,142 | B1 * | 1/2002 | Basey .................. | C07K 1/18 424/133.1 |
| 2012/0178910 | A1 | 7/2012 | Arunakumari et al. | |
| 2012/0202974 | A1 * | 8/2012 | Eon-Duval .............. | C07K 1/18 530/387.1 |

FOREIGN PATENT DOCUMENTS

| | | | |
|---|---|---|---|
| KR | 10-2008-0017322 A | 2/2008 | |
| KR | 10-2010-0086015 A | 7/2010 | |
| KR | 10-2013-0114209 A | 10/2013 | |
| WO | WO-2006125599 A2 * | 11/2006 | .......... B01D 15/362 |
| WO | 2013/089477 A1 | 6/2013 | |

* cited by examiner

Primary Examiner — Daniel E Kolker
Assistant Examiner — James L Rogers
(74) Attorney, Agent, or Firm — Baker & Hostetler LLP

(57) ABSTRACT

The present invention relates to a method for separating antibody isoforms using cation exchange chromatography and, more specifically, to a method for separating and purifying several isoforms, which are generated during an antibody production procedure, using a washing buffer for cation exchange chromatography.

6 Claims, 17 Drawing Sheets

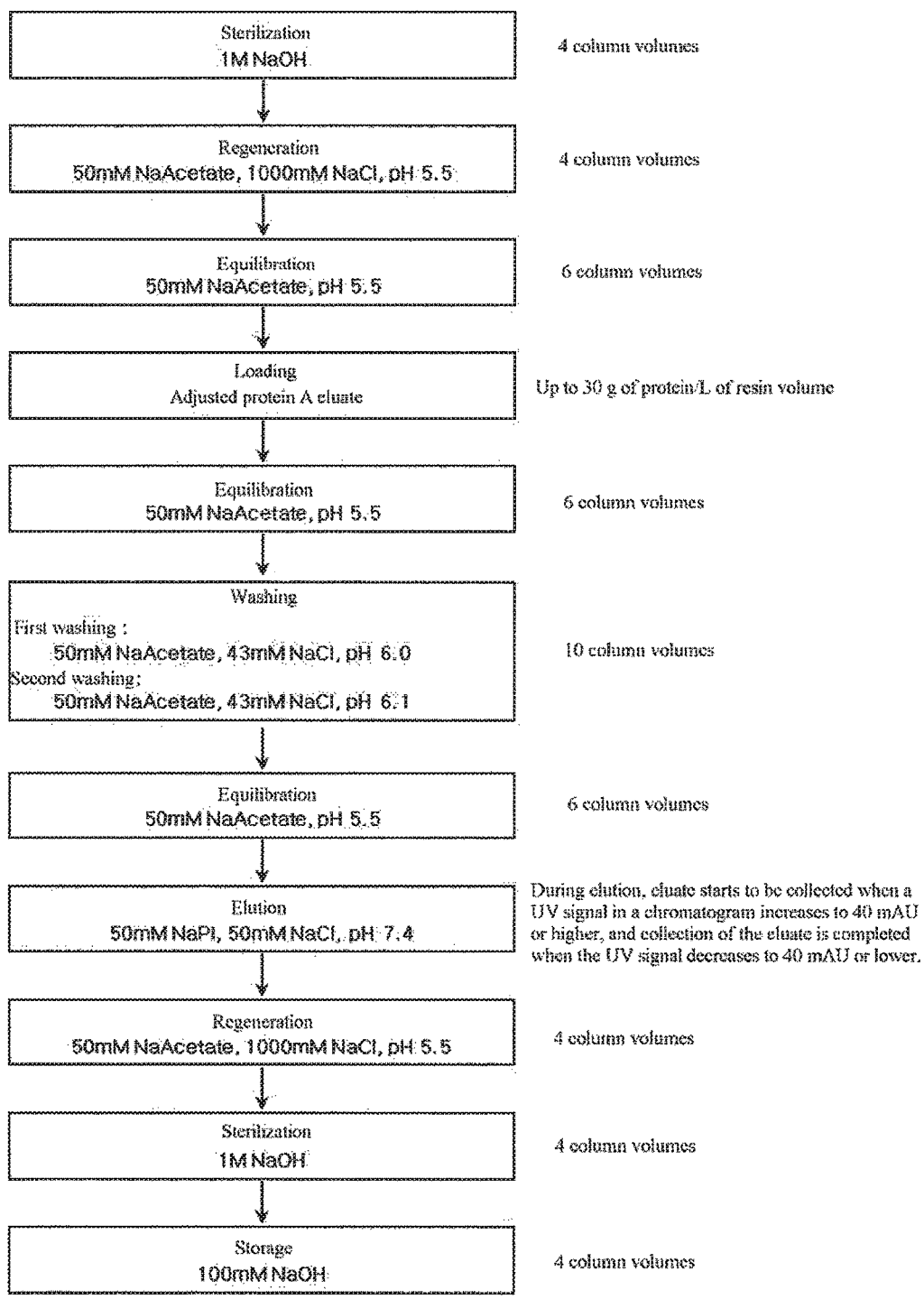

METHOD FOR SEPARATING ANTIBODY ISOFORMS USING CATION EXCHANGE CHROMATOGRAPHY

TECHNICAL FIELD

The present invention relates to a method for separating antibody isoforms using cation exchange chromatography, and more particularly, to a method for separating and purifying various antibody isoforms, produced in an antibody production process, using a buffer for cation exchange chromatography.

BACKGROUND ART

Proteins are expressed by genes in bacteria or cells. In the expression process, isoforms of the originally intended target protein can be produced due to glycosylation, glycation, or modifications caused by enzymes or other proteins, and isoforms can also be produced due to deamidation, oxidation, or substitution/deletion of amino acids, which is caused by external environmental stress. In the former case, isoforms are frequently produced by post-translational modifications during cell culture, and in the latter case, isoforms are frequently produced during the purification process or storage.

Isoforms produced as described above are classified into product-related substances and product-related impurities, according to how they maintain their medicinal effects compared to that of the originally intended target protein.

Monoclonal antibodies representative of protein therapeutic agents become a very attractive tool, because all the portions thereof associated with the ability to bind specifically to their targets can be used in vivo.

In the case of monoclonal antibodies, various types of isoforms are produced during expression of the antibodies in cells. In order to maximize the medicinal effects of such isoforms without producing product-related impurities, clone selection and culture processes are required to be developed to achieve this purpose. However, if isoforms corresponding to product-related impurities continue to remain, an effort is required so that these isoforms no longer increase during the purification process or storage.

Because product-related impurities have properties very similar to those of the desired product, it is very difficult to isolate these impurities by chromatography which is used in the purification process. However, with the recent development of technology, attempts have been made to remove such product-related impurities through development of new purification processes.

DISCLOSURE

Technical Problem

It is an object of the present invention to provide a method for separating antibody isoforms using cation exchange chromatography.

Another object of the present invention is to provide a method for producing an antibody preparation, including a purification process which uses the method for separating antibody isoforms.

Technical Solution

To achieve the above objects, an embodiment of the present invention provides a method for separating antibody isoforms, including the steps of:

a) loading an antibody-containing sample onto a cation exchange chromatography column equilibrated with an equilibration buffer;

b) washing the column with a washing buffer having a pH which is at least 1.0 lower than the pI of the antibody, the washing buffer having a salt concentration of 10-300 mM; and c) recovering a target antibody from the column using an elution buffer.

Another embodiment of the present invention provides a method for separating antibody isoforms, including the steps of:

a) loading an antibody-containing sample onto a cation exchange chromatography column equilibrated with an equilibration buffer having a pH which is at least 1.0 lower than the pI of the antibody, the equilibration buffer having a salt concentration of 10-300 mM; and b) recovering a target antibody from the column using an elution buffer.

Still another embodiment of the present invention provides a method for producing an antibody preparation, including a purification process which uses the method for separating antibody isoforms.

Hereinafter, the present invention will be described in further detail.

In an embodiment of the present invention, cation exchange chromatography is used to separate antibody isoforms.

As used herein, the term "ion exchange chromatography" means a chromatography method which uses a "ion exchange chromatography material". The "ion exchange chromatography material" means an immobile high-molecular-weight solid phase that carries covalently bound charged groups as chromatographical functional groups. For overall charge neutrality not covalently bound counter ions are associated therewith. The "ion exchange chromatography material" has the ability to exchange its not covalently bound counter ions for similarly charged ions of the surrounding solution. Depending on the charge of its exchangeable counter ions the "ion exchange chromatography material" is referred to as "cation exchange chromatography material" or as "anion exchange chromatography material". Further depending on the nature of the charged group the "ion exchange chromatography material" is referred to as e.g. in the case of cation exchange chromatography materials with sulfonic acid groups (S), or carboxymethyl groups (CM). Depending on the chemical nature of the charged group the "ion exchange chromatography material" can additionally be classified as strong or weak ion exchange chromatography material, depending on the strength of the covalently bound charged substituent. For example, strong cation exchange chromatography materials have a sulfonic acid group as chromatographic functional group and weak cation exchange chromatography materials have a carboxylic acid group as chromatographic functional group.

For example, "cation exchange chromatography materials", for example, are available under different names from a multitude of companies such as e.g. Bio-Rex, Macro-Prep CM (available from BioRad Laboratories, Hercules, Calif., USA), weak cation exchanger WCX 2 (available from Ciphergen, Fremont, Calif., USA), Dowex MAC-3 (available from Dow chemical company, Midland, Mich., USA), Mustang C (available from Pall Corporation, East Hills, N.Y., USA), Cellulose CM-23, CM-32, CM-52, hyper-D, and partisphere (available from Whatman plc, Brentford, UK), Amberlite IRC 76, IRC 747, IRC 748, GT 73 (available from Tosoh Bioscience GmbH, Stuttgart, Germany), CM 1500, CM 3000 (available from BioChrom Labs, Terre Haute, Ind., USA), and CM-Sepharose Fast Flow (available from GE Healthcare, Life Sciences, Germany). In addition, commercially available cation exchange resins further include carboxymethyl-cellulose, Bakerbond ABX, sulphopropyl (SP) immobilized on agarose (e.g. SP-Sepharose Fast Flow or SP-Sepharose High Performance, available from GE Healthcare—Amersham Biosciences Europe GmbH, Freiburg, Germany) and sulphonyl immobilized on agarose (e.g. S-Sepharose Fast Flow available from GE Healthcare, Life Sciences, Germany).

The "cation exchange chromatography materials" include mixed-mode chromatography materials performing a combination of ion exchange and hydrophobic interaction technologies (e.g., Capto adhere, Capto MMC, MEP HyperCell, Eshmuno HCX, etc.), mixed-mode chromatography material s performing a combination of anion exchange and cation exchange technologies (e.g., hydroxyapatite, ceramic hydroxyapatite, etc.), and the like. Cation exchange chromatography materials that may be used in cation exchange chromatography in the present invention may include, but are not limited to, all the commercially available cation exchange chromatography materials as described above. In an example of the present invention, CM-Sepharose Fast Flow and Capto S were used as cation exchange chromatography materials.

General chromatographic methods and their use are known to a person skilled in the art.

In an embodiment of the present invention, the method for separating antibody isoforms according to the present invention includes the steps of:

a) loading an antibody-containing sample onto a cation exchange chromatography column equilibrated with an equilibration buffer;

b) washing the column with a washing buffer having a pH which is at least 1.0 lower than the pI of the antibody, the washing buffer having a salt concentration of 10-300 mM; and c) recovering a target antibody from the column using an elution buffer.

In step b), the pH of the washing buffer may be 5.0 to 8.0, but is not limited thereto.

In addition, in step b), the conductivity of the washing buffer may be 0.5 to 50 mS/cm, but is not limited thereto.

The antibody isoforms may be acidic isoforms. In an example of the present invention, it could be found by CEX-HPLC analysis that acidic antibody isoforms were separated by the washing method.

The antibody-containing sample in step a) may be adjusted to a conductivity of 10 mS/cm or lower before loading. The conductivity may be adjusted by any one salt selected from the group consisting of sodium citrate, sodium acetate, sodium chloride, sodium phosphate, sodium sulfate, potassium chloride, potassium sulfate, potassium phosphate, Tris, MES (2-(N-morpholino)ethanesulfonic acid), HEPES (4-(2-hydroxyethyl)-1-piperazineethanesulfonic acid), and CHAPS (3-[(3-cholamidopropyl)-dimethylammonio]-1-propane sulfonate), but is not limited thereto.

In an embodiment of the present invention, the method may further include, before step a) or after step c), a step of loading and purifying the antibody-containing sample on any one chromatography column selected from the group consisting of a protein A affinity chromatography column, an ion exchange chromatography column, a hydrophobic interaction chromatography column and a mixed-mode chromatography column. In an example of the present invention, before step a), a step of purifying an anti-EGFR antibody or anti-CD20 antibody-containing sample by protein A affinity chromatography was additionally performed.

In step b), the washing buffer may be any one selected from the group consisting of sodium citrate, sodium acetate, sodium chloride, sodium phosphate, sodium sulfate, potassium chloride, potassium sulfate, potassium phosphate, Tris, MES (2-(N-morpholino)ethanesulfonic acid), HEPES (4-(2-hydroxyethyl)-1-piperazineethanesulfonic acid, and CHAPS(3-[(3-cholamidopropyl)-dimethylammonio]-1-propane sulfonate), but is not limited thereto.

In step a), the equilibration buffer may be any one selected from the group consisting of sodium citrate, sodium acetate, sodium chloride, sodium phosphate, sodium sulfate, potassium chloride, potassium sulfate, potassium phosphate, Tris, MES (2-(N-morpholino)ethanesulfonic acid), HEPES (4-(2-hydroxyethyl)-1-piperazineethanesulfonic acid, and CHAPS(3-[(3-cholamidopropyl)-dimethylammonio]-1-propane sulfonate), but is not limited thereto.

In step a), the pH of the equilibration buffer may be 8.5 or less, but is not limited thereto.

In step a), the concentration of the equilibration buffer may be 100 mM or less, but is not limited thereto.

In step a), the conductivity of the equilibration buffer may be 15 mS/cm or less, but is not limited thereto.

In step c), the elution buffer may be any one selected from the group consisting of sodium citrate, sodium acetate, sodium chloride, sodium phosphate, sodium sulfate, potassium chloride, potassium sulfate, potassium phosphate, Tris, MES (2-(N-morpholino)ethanesulfonic acid), HEPES (4-(2-hydroxyethyl)-1-piperazineethanesulfonic acid, and CHAP S(3-[(3-cholamidopropyl)-dimethylammonio]-1-propane sulfonate), but is not limited thereto.

In step c), the pH of the elution buffer may be 4.0 or more, but is not limited thereto.

In step c), the concentration of the elution buffer may be 20 mM or more, but is not limited thereto.

In step c), the conductivity of the elution buffer may be 5 mS/cm or more, but is not limited thereto.

In an embodiment of the present invention, the antibody may be anti-EGFR (epidermal growth factor receptor) antibody, anti-CD20 antibody, anti-HER2 antibody, anti-TNFα antibody, anti-VEGF (vascular endothelial growth factor) antibody, anti-influenza A virus antibody, anti-RSV (Respiratory Syncytial Virus) antibody, anti-HBV (Hepatitis B Virus) antibody, anti-rabies virus antibody, but is not limited thereto. In other words, the present invention may generally be carried out using immunoglobulins. Each of the antibodies may be obtained by introducing and expressing a polynucleotide encoding each of the antibodies in mammalian cells. The methods for producing the antibodies are well known in the art, and thus the description thereof is omitted herein.

Another embodiment of the present invention provides a method for separating antibody isoforms, including the steps of:

a) loading an antibody-containing sample onto a cation exchange chromatography column equilibrated with an equilibration buffer having a pH which is at least 1.0 lower than the pI of the antibody, the equilibration buffer having a salt concentration of 10-300 mM; and b) recovering a target antibody from the column using an elution buffer.

In other words, even when the pH and salt concentration conditions of the above-described washing buffer are applied to the loading conditions of the cation exchange chromatography column, antibody isoforms can be separated in the same or similar manner.

Still another embodiment of the present invention provides a method for separating antibody isoforms, including the steps of:

a) loading an antibody-containing sample onto a cation exchange chromatography column equilibrated with an equilibration buffer; and b) recovering a target antibody from the column by increasing pH or salt concentration from a low pH or salt concentration to a high pH or salt concentration by a linear gradient with an elution buffer having either a pH which is at least 1.0 lower than a pI of the antibody or a salt concentration of 10-300 mM.

In step b), the linear pH gradient of the elution buffer may range from pH 5.0 to 8.0, from pH 6.0 to 8.0, or from pH 7.0 to 8.0, but is not limited thereto. In an example of the present invention, the target antibody was eluted by a linear pH gradient from pH 6.0 to 8.0.

In step b), the linear salt concentration gradient of the elution buffer may range from 10 to 300 mM, from 20 to 300 mM, from 30 to 300 mM, from 40 to 300 mM, from 50 to 300 mM, from 60 to 300 mM, from 70 to 300 mM, from 80 to 300 mM, from 90 to 300 mM, from 100 to 300 mM, from 150 to 300 mM, or from 200 to 300 mM, but is not limited thereto. In addition, the linear salt concentration gradient of the elution buffer in step b) may range from 10 to 200 mM, from 20 to 200 mM, from 30 to 200 mM, from 40 to 200 mM, from 50 to 200 mM, from 60 to 200 mM, from 70 to 200 mM, from 80 to 200 mM, from 90 to 200 mM, from 100 to 200 mM, or from 150 to 200 mM, but is not limited thereto. In an example of the present invention, the target protein was eluted by a linear salt concentration gradient from 50 to 200 mM.

In addition, in step b), the target antibody may be eluted by applying a linear gradient to both the pH and salt concentration of the elution buffer.

The terms "antibody" and "immunoglobulin", which may interchangeably be used herein, generally include at least two light-chain polypeptides and two heavy-chain polypeptides. Each of the heavy-chain and light-chain polypeptides contains a variable region (generally the amino terminal portion of the polypeptide chain) which contains a binding region that is able to interact with an antigen. In addition, each of the heavy-chain and light-chain polypeptides includes a constant region (generally the carboxyl terminal portion) which may mediate the binding of the antibody to host tissue or factors including various cells of the immune system, some phagocytic cells and a first component (C1q) of the classical complement system. As used herein, the term "antibody" or "immunoglobulin" refers to a protein consisting of one or more polypeptides substantially encoded by antibody genes. The recognized antibody genes include the different constant region genes as well as the myriad antibody variable region genes. Antibodies may exist in a variety of forms, including, for example, Fv, Fab, and $F(ab)_2$ as well as single chains. For example, antibodies according to an embodiment of the present invention include monoclonal antibodies and fragments thereof, for example, isolated heavy or light chains, or heavy or light chains consisting only of constant regions, as well fragments thereof.

As used herein, the term "isoforms" means proteins having forms slightly different from the desired form due to post-transcriptional modification, post-translational modification and cellular differences, among the same types of proteins expressed from the same gene. Such isoforms can be classified as product-related substances or product-related impurities according to the function and purpose of the original protein.

As used herein, the term "antibody isoforms" means those limited to antibodies among the proteins described above with respect to "isoforms".

As known to date, the causes of post-translational modification of antibodies are as shown in Table 1 below.

TABLE 1

| Causes of post-translational modification of antibodies | |
|---|---|
| Aggregation | Fragmentation |
| Conformation variant | Glycation |
| C-terminal lysine variant | Glycosylation |
| Deamidation | Oxidation |
| Disulfide bond | Thioether link |

As used herein, the term "impurities" includes any substances other than the target protein. Examples of impurities include, but are not limited to, protein isoforms having no medicinal effect, protein aggregates, protein fragments, DNA contaminants, virus, protein A (eluted from a column), host cell proteins, endotoxins, medium components such as Hy-Fish (FL) and IGF, and the like.

Advantageous Effects

According to the present invention, antibody isoforms can be effectively separated by cation exchange chromatography. Thus, the method of the present invention can be used for high-purity separation of antibodies produced from animal cell cultures by gene recombination technology.

DESCRIPTION OF DRAWINGS

FIGS. 2a, 2b and 2c were produced by single-step gradient washing at ratios of 70:30, 65:35, and 60:40, respectively.

FIG. 7 shows a step of purifying an antibody using weak cation exchange chromatography according to still another embodiment of the present invention.

BEST MODE

Hereinafter, the present invention will be described in further detail with reference to examples. It is to be understood, however, that these examples are for illustrative purposes only and are not intended to limit the scope of the present invention.

EXAMPLES

Example 1

Purification of Anti-EGFR Monoclonal Antibody by Protein A Affinity Chromatography In a first step, anti-EGFR monoclonal antibody was purified by protein A affinity chromatography. Elution from the protein A column was performed under acidic conditions (50 mM sodium acetate, 60 mM sodium chloride buffer, pH 3.5±0.05). Before filtration, the pH of the solution was adjusted to 5.0 using 1M Tris buffer, and the solution was diluted with water to adjust the conductivity to 2 mS/cm or less. The protein A eluate is a solution having a protein concentration of 0.3-10 mg/ml and obtained by buffering with sodium acetate and Tris and dilution with water. Hereinafter, the material will be referred to as "adjusted protein A eluate" prepared for loading onto a cation exchange chromatography column.

Example 2

Separation of Anti-EGFR Monoclonal Antibody Isoforms by Cation Exchange Chromatography 2-1: Separation of Anti-EGFR Monoclonal Antibody Isoforms by Weak Cation Exchange Chromatography The protein A eluate adjusted by the method of Example 1 was loaded onto weak cation exchange chromatography resin (CM Sepharose Fast Flow, GE Healthcare) to thereby separate various isoforms of anti-EGFR monoclonal antibody (pI: 7.9-8.8).

*Chromatography Conditions:
Resin: CM Sepharose Fast Flow
Flow rate: 200 cm/h
Equilibration: 20 mM Na Acetate, pH 5.0 buffer
Loading: up to 20 g of protein/L of resin volume
Sterilization: 1 M NaOH solution
Regeneration: 20 mM Na Phosphate, 1000 mM NaCl, pH 7.0 buffer
Washing: single-step gradient
Elution: 50 mM Na Acetate, 100 mM NaCl, pH 5.5

Figure 1:
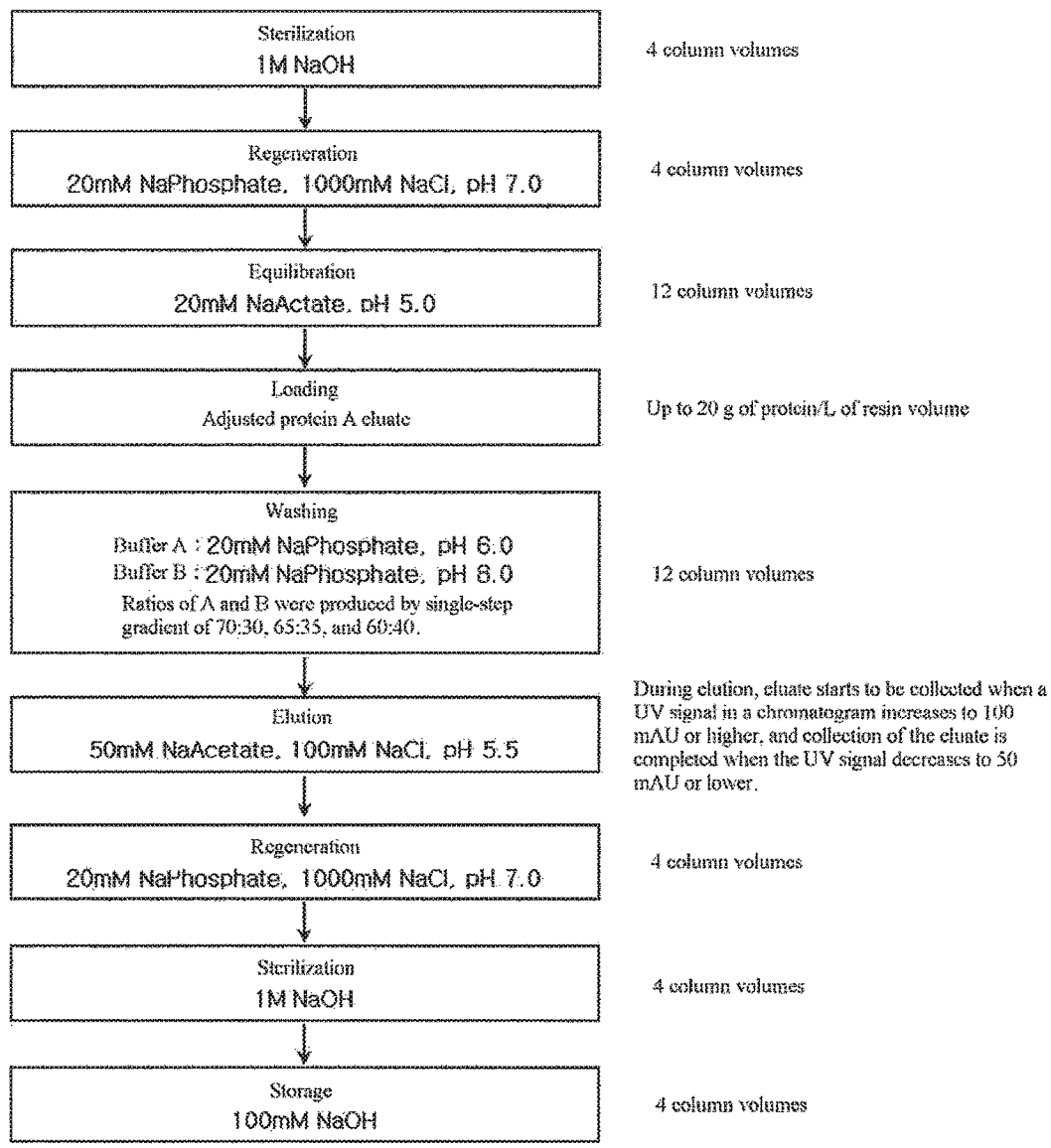
FIG. 1 shows a step of purifying an antibody using weak cation exchange chromatography according to an embodiment of the present invention.

The experiment was performed according to the procedure shown in FIG. 1. The adjusted protein A eluate was loaded onto a cation exchange chromatography column, and the monoclonal antibody bound to the column was washed with 12 column volumes of buffer by three single-step gradient methods. For elution, when the UV signal increased to 100 mAU, the product started to be collected, and when the UV signal decreased by 50 mAU, the product collection was completed.

For washing, a washing method by a single-step gradient at varying ratios of buffer A (20 mM Na Phosphate, pH 6.0) to buffer B (20 mM Na Phosphate, pH 8.0) was used. The ratios of buffer A: buffer B in washing were 70:30, 65:35, and 60:40, respectively.

Figure 2A:
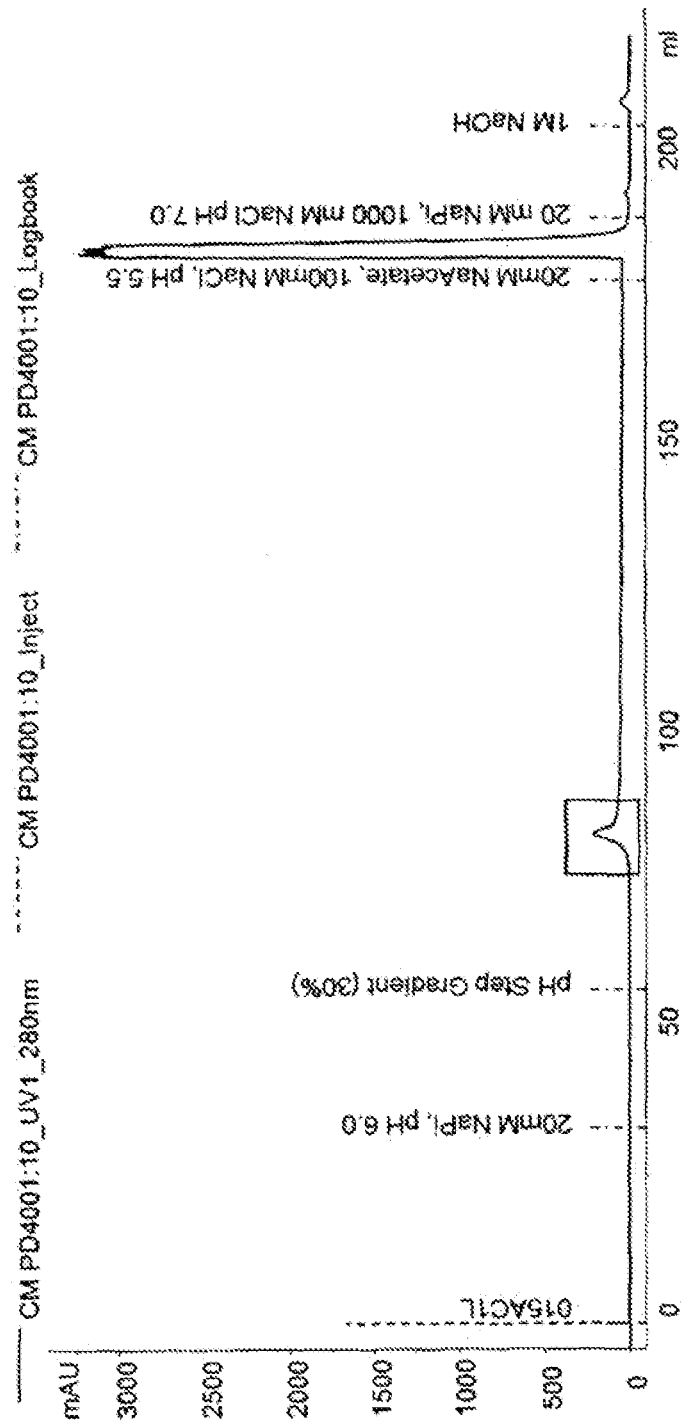
FIGS. 2a to 2c show chromatograms obtained by single-step gradient washing at varying ratios of buffer A (20 mM Na phosphate, pH 6.0) to buffer B (20 mM Na phosphate, pH 8.0) according to an embodiment of the present invention.
Figure 2B:
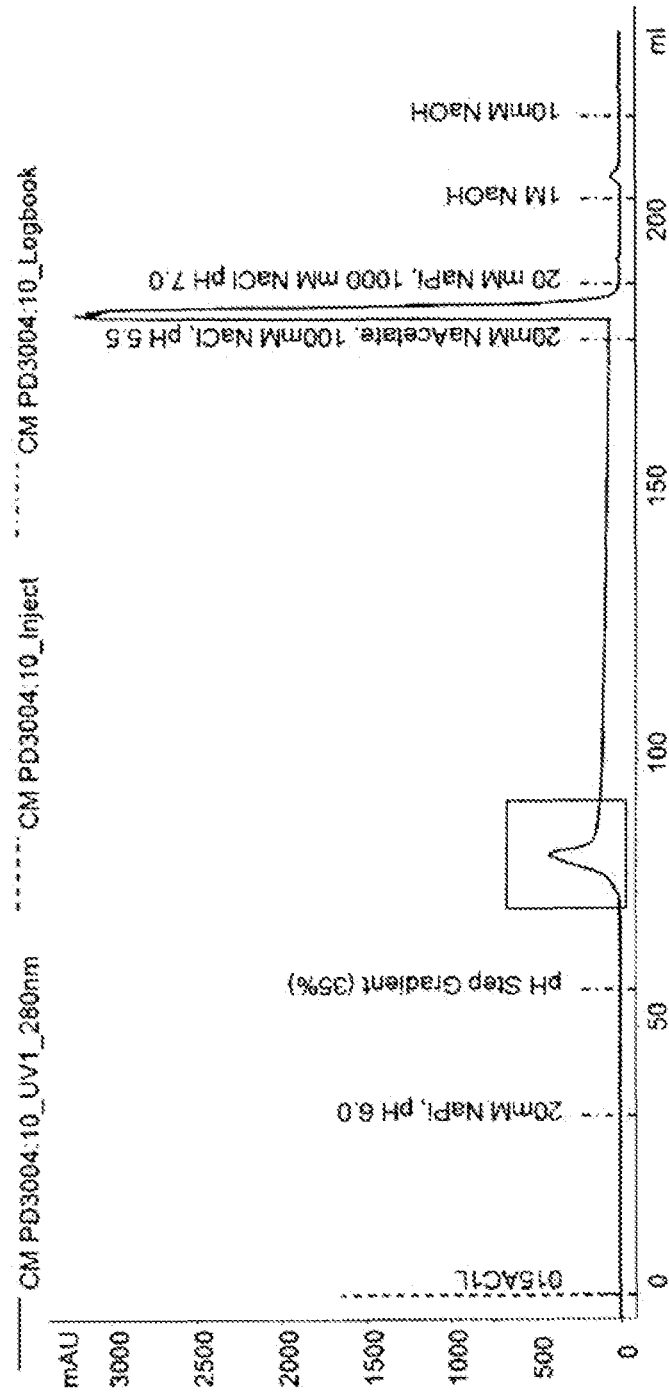
Figure 2C:
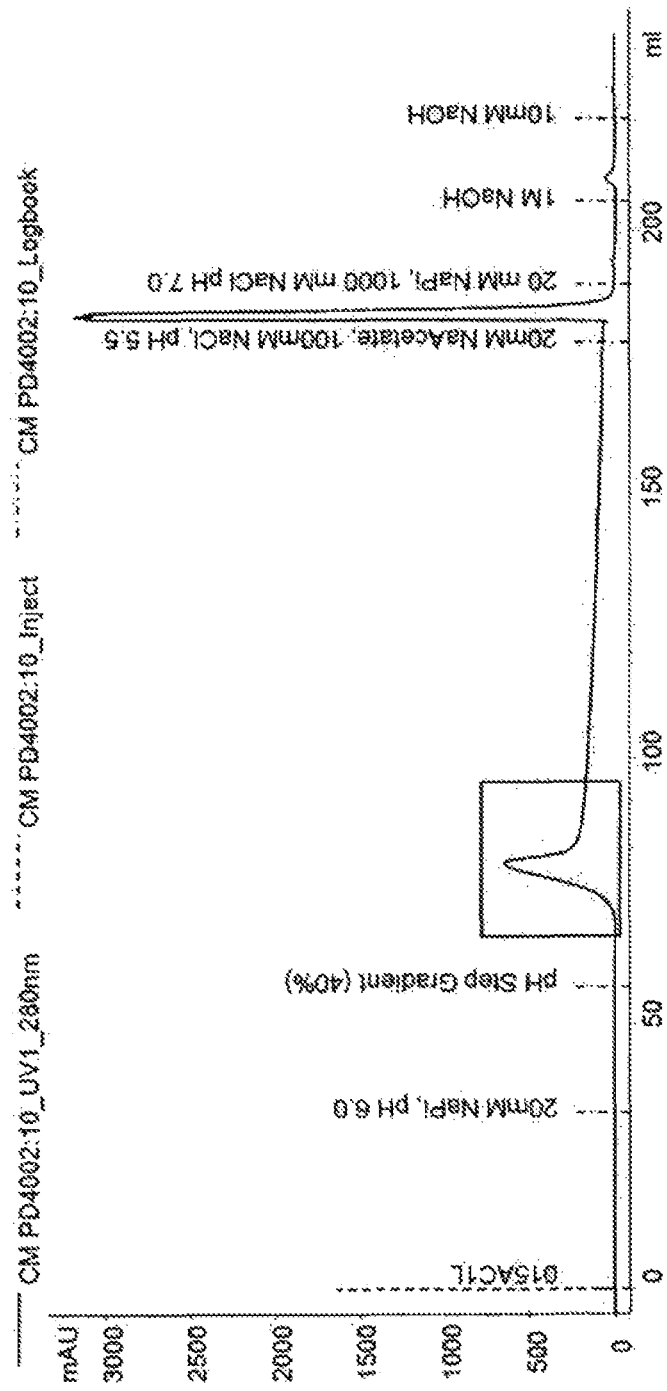

The chromatogram shown in FIG. 2a was produced by single-step gradient washing at a ratio of 70:30, and the chromatograms shown in FIGS. 2b and 2c were produced by single-step gradient washing at ratios of 65:35 and 60:40, respectively. As can be seen in the chromatograms, the UV signal increased in the washing step, suggesting that isoforms weakly attached to the cation exchange resin were detached in the washing step.

After single-step gradient washing at ratios of 70:30, 65:35 and 60:40, the monoclonal antibody separated by elution was analyzed by CEX-HPLC, and the glycans in the Fab portion of the monoclonal antibody were analyzed by intact mass analysis with LC/MS. The results of the analysis are shown in Tables 2 and 3 below.

TABLE 2

Results of analysis of yield caused by single-step gradient washing and CEX-HPLC analysis

| Analytical sample | | Yield (%) | Acidic peak (%) (peak 1 + 2 + 3) |
|---|---|---|---|
| Adjusted protein A eluate | | N/A | 39.48% |
| Single-step gradient (buffer A:buffer B) | 70:30 | 70.49% | 29.18% |
| | 65:35 | 50.37% | 14.82% |
| | 60:40 | 33.90% | 4.06% |

TABLE 3

| | 4GlcNAc, 3Hex, F | 4GlcNAc, 4Hex, F | 4GlcNAc, 5Hex, F | 4GlcNAc, 6Hex, F | 4GlcNAc, 7Hex, F | 4GlcNAc, 6Hex, F, NGNA | 5GlcNAc, 7Hex, F |
|---|---|---|---|---|---|---|---|
| Sample ID | G0F | G1F | G2F | G2F + 1aGal | G2F + 2aGal | G2F + 1aGal + 1NGNA | — |
| Adjusted protein A eluate | 2.5 | 2.0 | 2.9 | 4.6 | 20.8 | 26.7 | 2.6 |
| Single gradient washing at 70:30 | 3.4 | 2.6 | 3.5 | 5.2 | 22.3 | 26.0 | 2.7 |
| Single gradient washing at 65:35 | 4.5 | 3.4 | 4.6 | 5.4 | 25.8 | 23.6 | 2.6 |
| Single gradient washing at 60:40 | 6.6 | 4.9 | 5.3 | 5.5 | 28.4 | 19.8 | 2.7 |

| | 4GlcNAc, 5Hex, F, 2NGNA | 5GlcNAc, 8Hex, F | 5GlcNAc, 9Hex, F | 5GlcNAc, 8Hex, F, NGNA | 5GlcNAc, 7Hex, F, 2NGNA | |
|---|---|---|---|---|---|---|
| Sample ID | G2F + 2NGNA | — | — | — | — | Sum |
| Adjusted protein A eluate | 9.0 | 2.6 | 9.5 | 12.7 | 4.2 | 100.0 |
| Single gradient washing at 70:30 | 6.2 | 2.6 | 10.9 | 11.9 | 2.6 | 100.0 |

TABLE 3-continued

| | | | | | | |
|---|---|---|---|---|---|---|
| Single gradient washing at 65:35 | 3.8 | 2.5 | 11.9 | 10.6 | 1.2 | 100.0 |
| Single gradient washing at 60:40 | 2.4 | 2.4 | 13.2 | 8.2 | 0.4 | 100.0 |

From the CEX-HPLC analysis results in Table 2 above, it can be seen that acidic portions among isoforms of the material before loading onto the cation exchange chromatography column were separated by the pH of the washing buffer. In order to understand the cause by which such isoforms were produced, the Fab portion was analyzed by intact mass with LC/MS (Table 3), and as a result, it could be seen that the portion including NGNA (N-glycolylneuraminic acid) was removed from the glycans of the Fab by washing, and then eluted. Because NGNA has a negatively charged structure, it can be seen that the acidic portion analyzed by CEX-HPLC includes isoforms including such NGNA.

2-2: Separation of Anti-EGFR Monoclonal Antibody Isoforms by Strong Cation Exchange Chromatography The adjusted protein A eluate prepared according to the process of Example 1 was loaded onto strong cation exchange chromatography resin (Capto S, GE Healthcare) to thereby separate various isoforms of anti-EGFR monoclonal antibody (pI: 7.9-8.8).

*Chromatography Conditions:
Resin: Capto S
Flow rate: 300 cm/h
Equilibration: 50 mM Na Acetate, pH 5.5 buffer
Loading: up to 10 g of protein/L of resin volume
Sterilization: 1M NaOH solution
Regeneration: 20 mM Na Phosphate, 1000 mM NaCl, pH 7.0 buffer
Washing: see Table 4 below
Elution: 50 mM Na Acetate, 100 mM NaCl, pH 5.5

Figure 3:
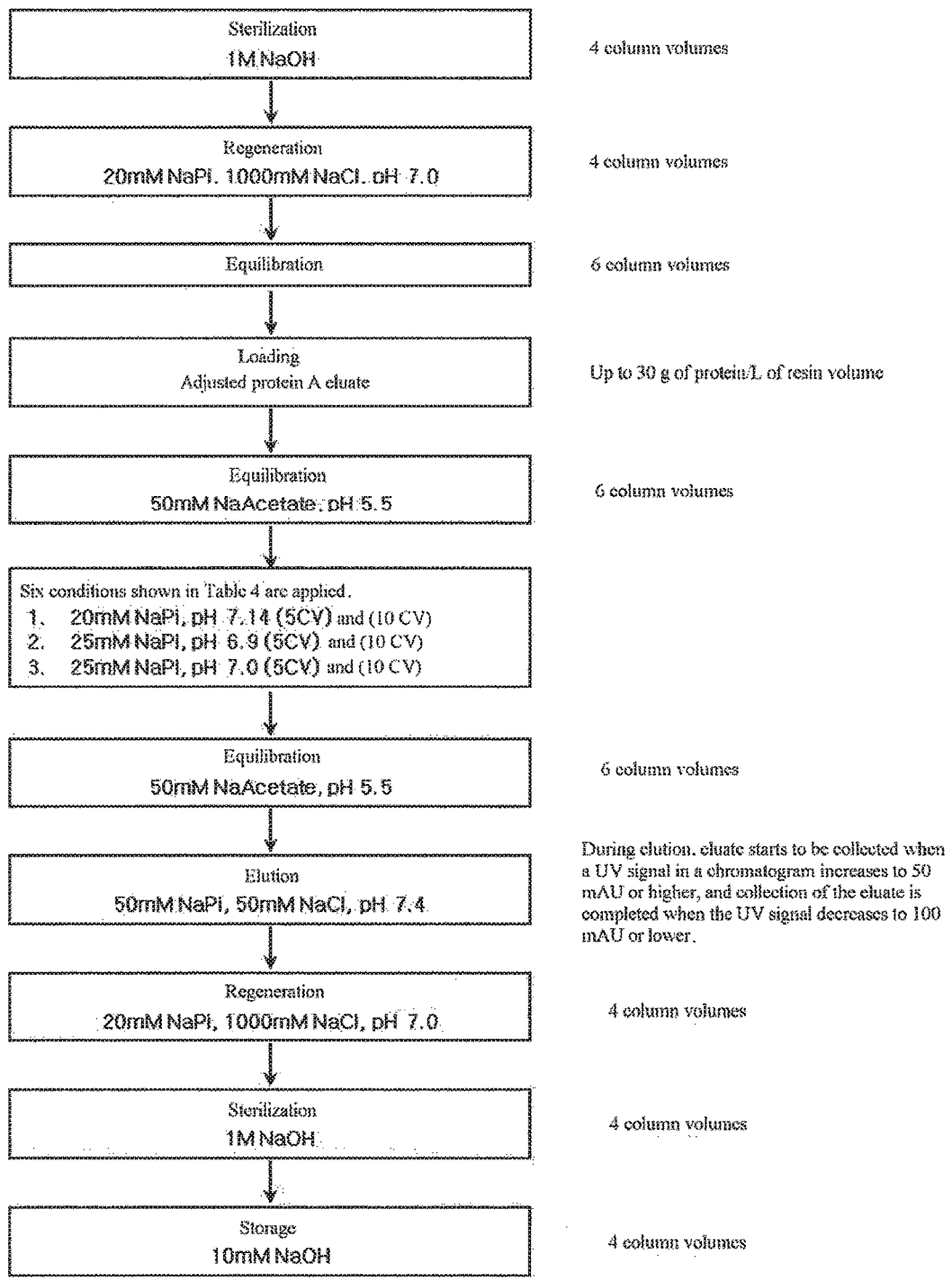
FIG. 3 shows a step of purifying an antibody using strong cation exchange chromatography according to an embodiment of the present invention.
Figure 4A:
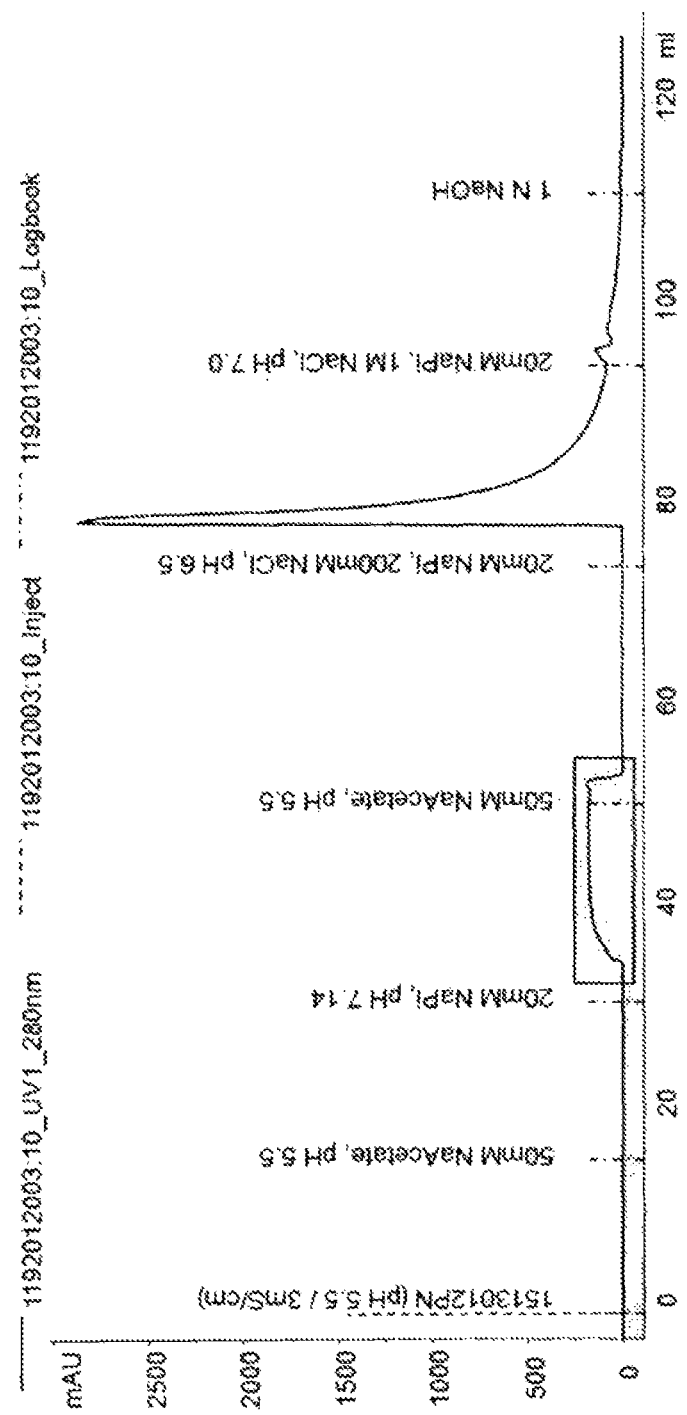
FIGS. 4a to 4f show chromatograms obtained using each of the washing buffer conditions shown in Table 4 according to an embodiment of the present invention.
Figure 4B:
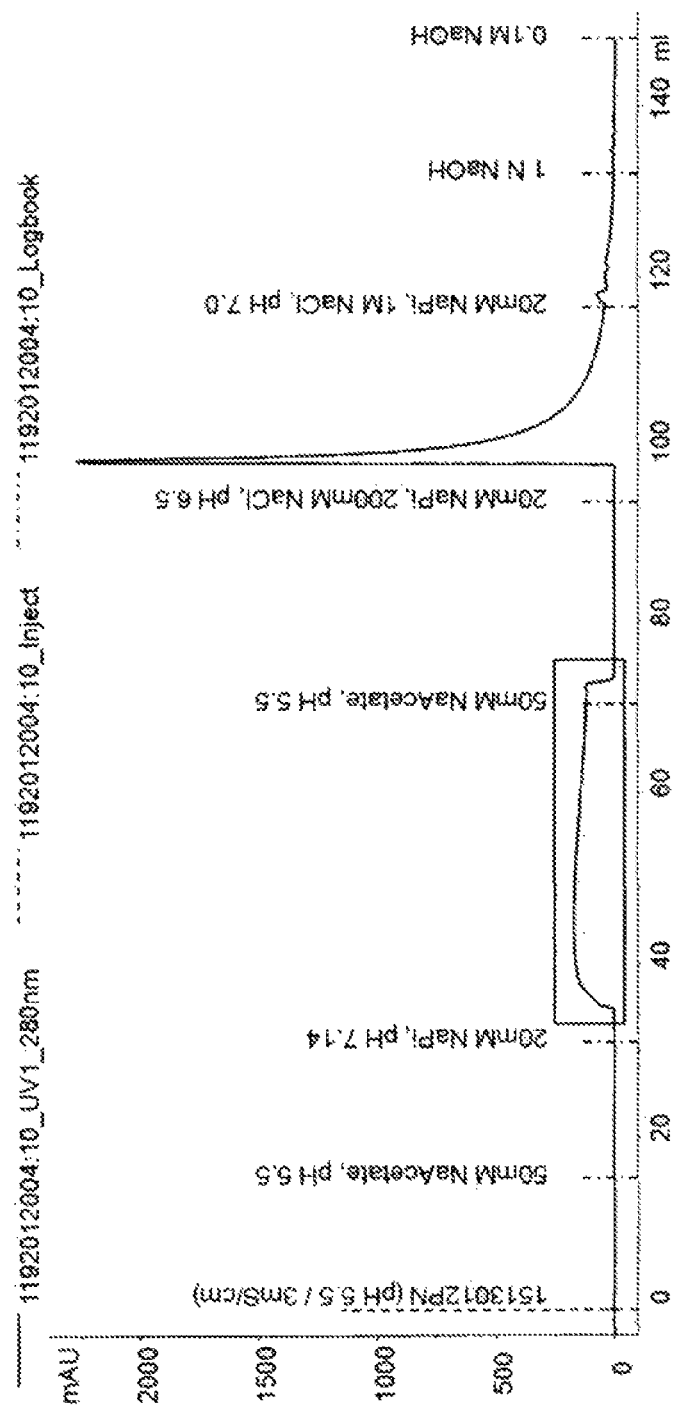
Figure 4C:
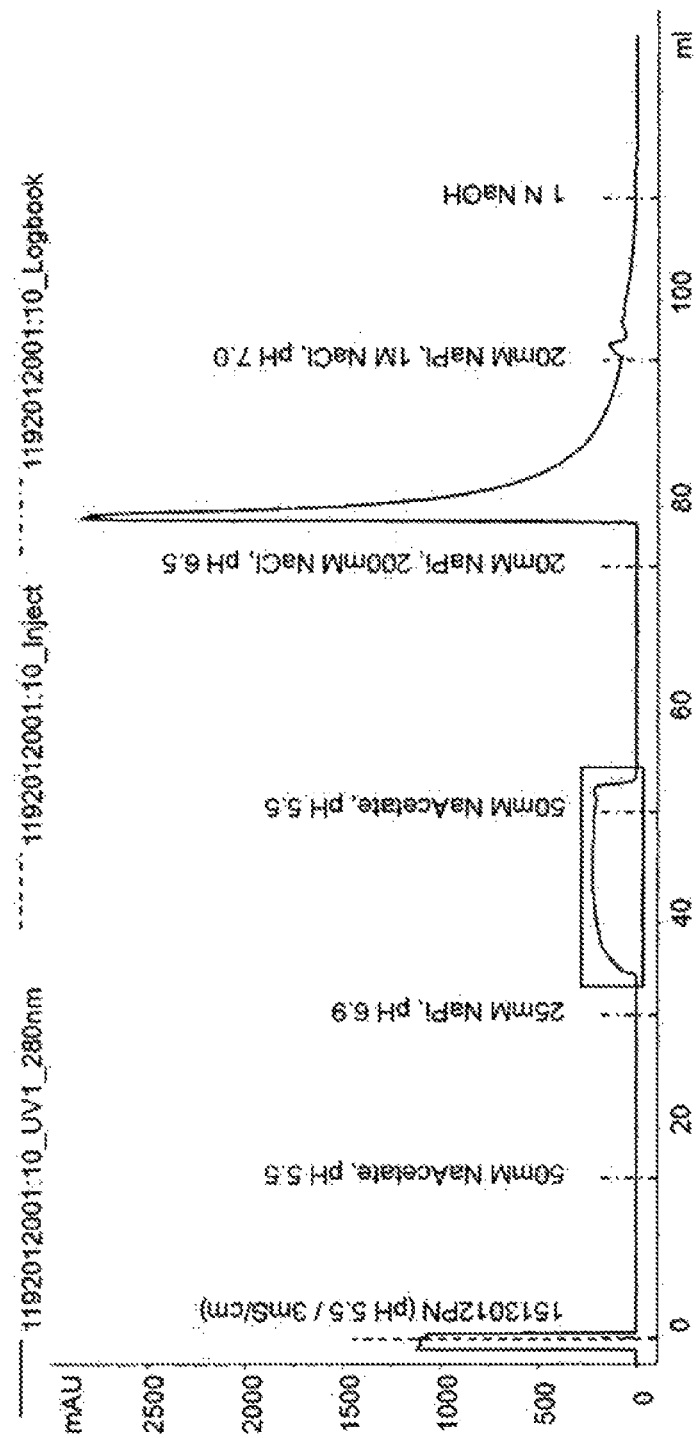
Figure 4D:
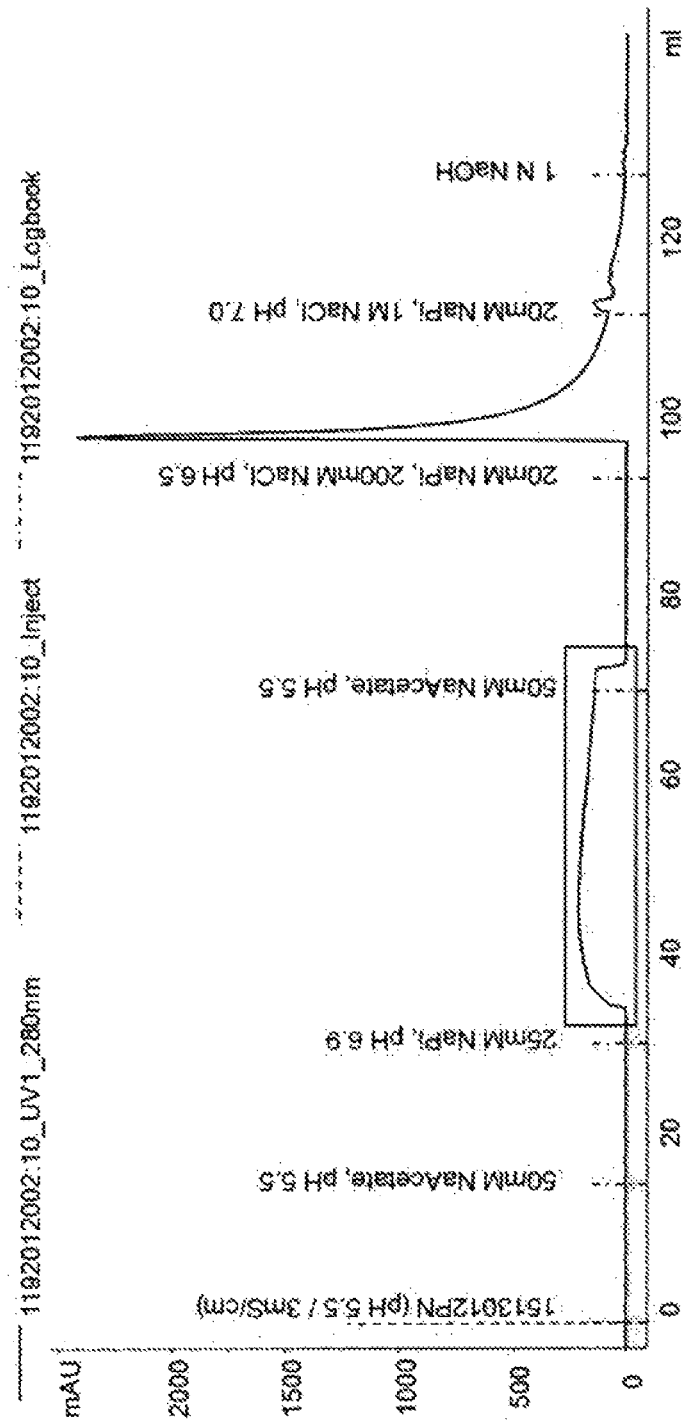
Figure 4E:
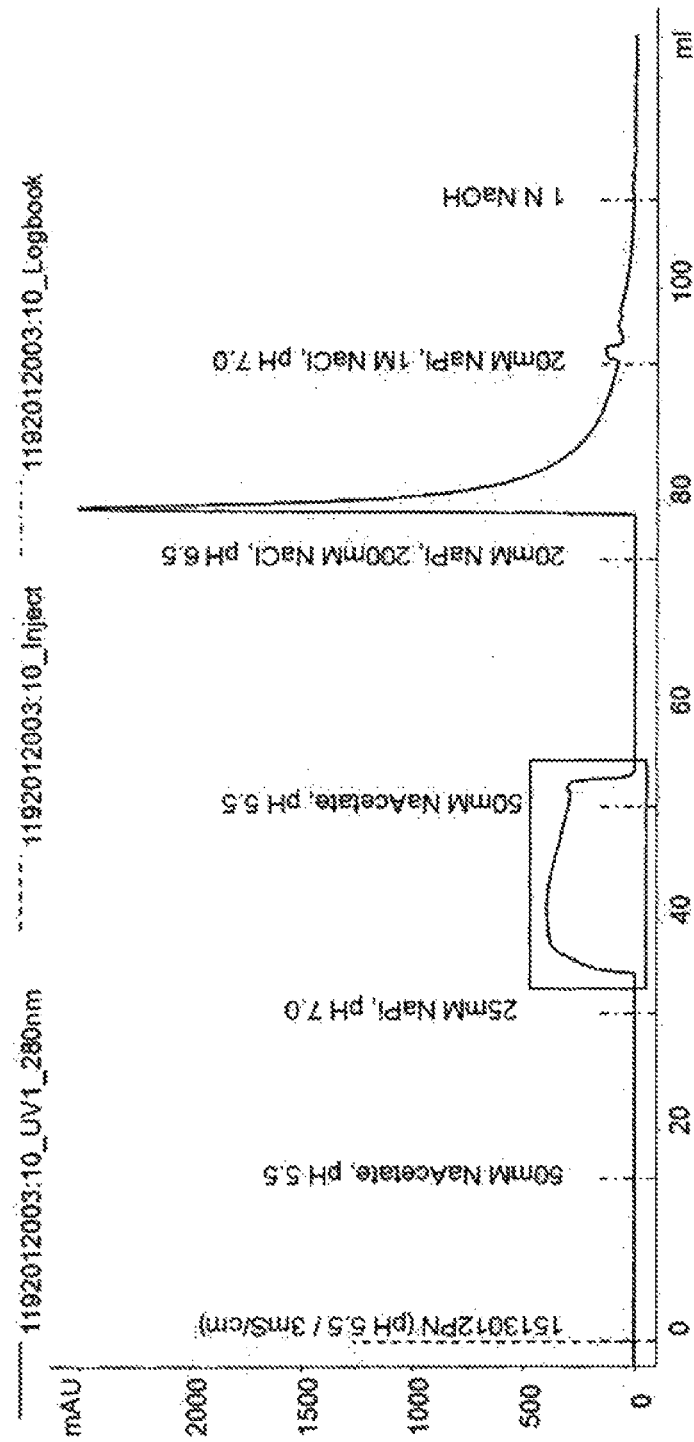
Figure 4F:
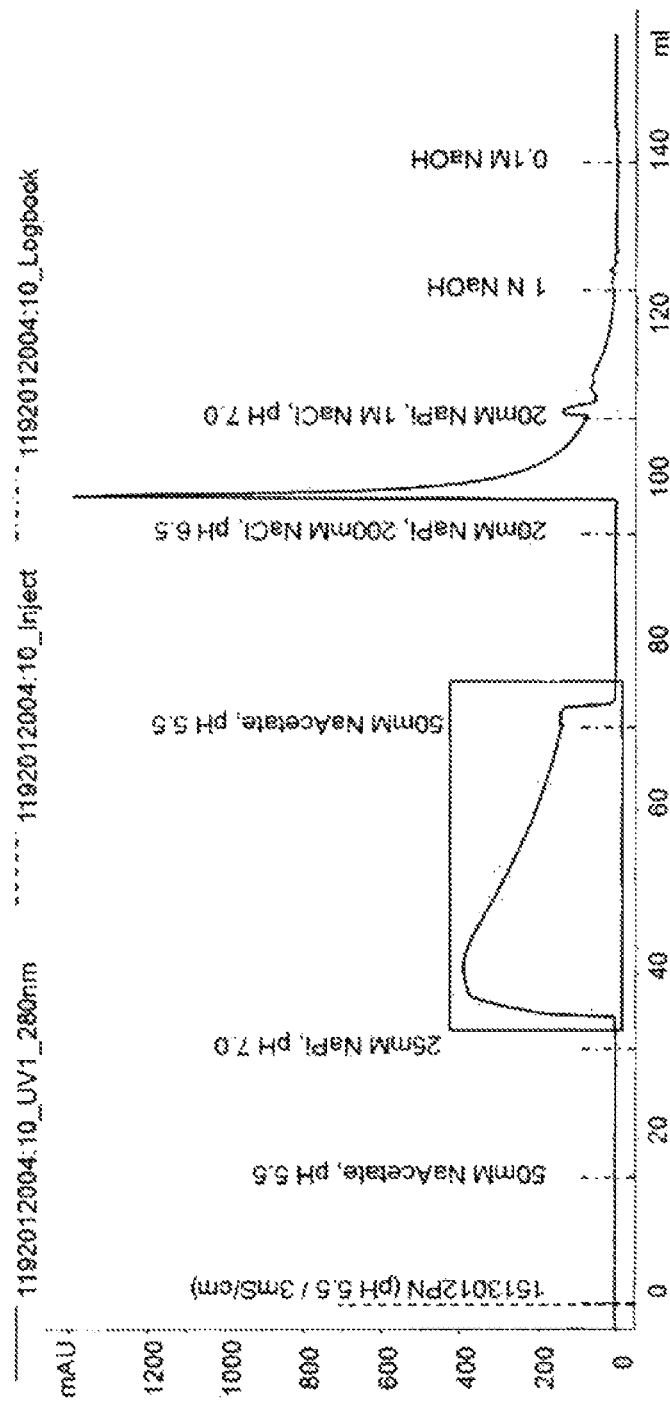

The experiment was performed according to the procedure shown in FIG. 3. The adjusted protein A eluate was loaded onto a cation exchange chromatography column, and the monoclonal antibody bound to the column was washed with each of 5 column volumes of buffer and 12 column volumes of buffer under three washing conditions. For elution, when the UV signal increased to 50 mAU, the product started to be collected, and when the UV signal decreased by 100 mAU, the product collection was completed.

TABLE 4

Washing buffer conditions and wash volumes

| Experiment No. | Washing conditions | Wash volumes (column volumes) |
|---|---|---|
| CS1E | 20 mM NaPi, pH 7.14 | 5 |
| CS2E | | 10 |
| CS3E | 25 mM NaPi, pH 6.9 | 5 |
| CS4E | | 10 |
| CS5E | 25 mM NaPi, pH 7.0 | 5 |
| CS6E | | 10 |

Six experiments (from CS1E to CS6E) produced the chromatograms shown in FIGS. 4a to 4f, respectively. Referring to the chromatograms, it can be seen that the UV signal increased in the washing step, like the case of Example 1, suggesting that isoforms weakly attached to the cation exchange resin were detached.

After washing in each experiment, the monoclonal antibody separated by elution was analyzed by CEX-HPLC to determine whether isoforms were separated.

TABLE 5

Results of analysis of yield caused by single-step gradient washing and CEX-HPLC analysis

| Analytical sample | | Yield (%) | Acidic peak (%) (peak 1 + 2 + 3) |
|---|---|---|---|
| Adjusted protein A eluate | | N/A | 25.20% |
| Washing conditions (wash volume) | 20 mM NaPi, pH 7.14 (5CV) | 69.68% | 14.48% |
| | 20 mM NaPi, pH 7.14 (10CV) | 40.76% | 5.32% |
| | 25 mM NaPi, pH 6.9 (5CV) | 65.66% | 12.66% |
| | 25 mM NaPi, pH 6.9 (10CV) | 42.83% | 6.54% |
| | 25 mM NaPi, pH 7.0 (5CV) | 45.43% | 11.44% |
| | 25 mM NaPi, pH 7.0 (10CV) | 19.19% | 5.37% |

From the CEX-HPLC analysis results in Table 5 above, it can be seen that acidic portions of isoforms of the material before loading onto the cation exchange chromatography column were separated depending on the washing buffer conditions and the wash volume, and thus the yield was reduced. Thus, it can be seen that the antibody isoforms were separated by Examples 2-1 and 2-2 in a controlled manner depending on the washing conditions regardless of the cationic intensity.

2-3: Separation of Anti-EGFR Monoclonal Antibody Isoforms Using Linear Concentration Gradient in Weak Cation Exchange Chromatography The adjusted protein A eluate prepared according to the method of Example 1 was loaded onto weak cation exchange chromatography resin (CM Sepharose Fast Flow, GE Healthcare) to thereby separate various isoforms of anti-EGFR monoclonal antibody (pI: 7.9-8.8).

*Chromatography conditions:
Resin: CM Sepharose Fast Flow
Flow rate: 200 cm/h
Equilibration: 20 mM Na Acetate, pH 5.0 buffer
Loading: 20 g of protein/L of resin volume
Sterilization: 1M NaOH solution
Regeneration: 20 mM Na Phosphate, 1000 mM NaCl, pH 7.0 buffer
Elution 1: Linear concentration gradient (see Table 6)
Elution 2: 50 mM Na Acetate, 100 mM NaCl, pH 5.5

Figure 5:
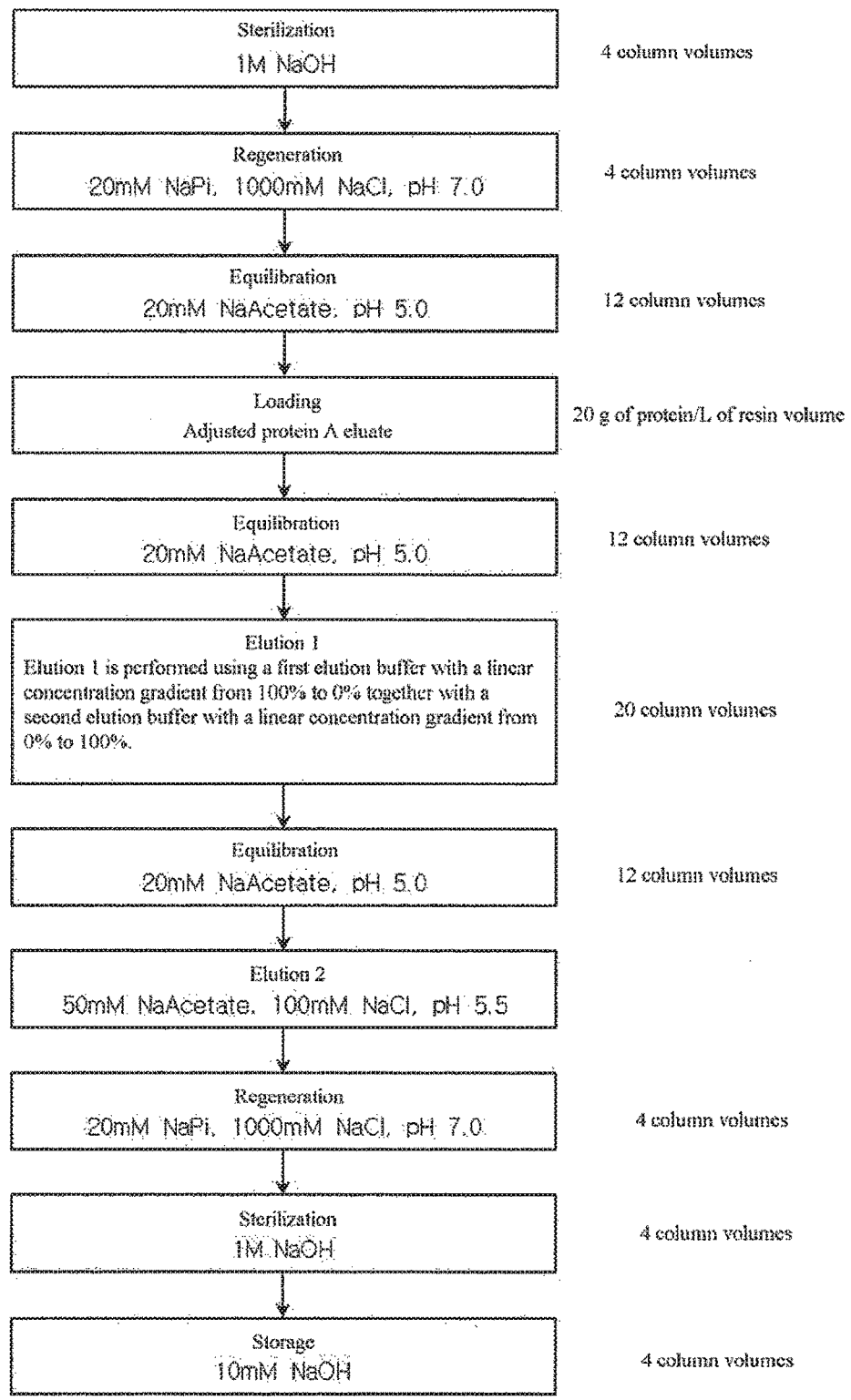
FIG. 5 shows a step of purifying an antibody using a linear concentration gradient in weak cation exchange chromatography according to another embodiment of the present invention.

The experiment was performed according to the procedure shown in FIG. 5. The adjusted protein A eluate was loaded onto a cation exchange column chromatography column, and first elution of the monoclonal antibody bound to the column was performed with 20 column volumes of buffer by two linear concentration gradient methods. To collect the monoclonal antibody remaining after the first elution, second elution was performed after equilibration. The second elution may be selectively performed according to the degree of the first elution.

The first elution was performed using a linear concentration gradient in which the concentration of buffer A was gradually decreased and the concentration of buffer B was gradually increased. Herein, the linear concentration gradient consisted of two linear gradients: a linear pH gradient, and a linear salt concentration gradient. The elution buffers used are shown in Table 6 below.

TABLE 6

Buffers used in linear concentration gradient

| | Linear concentration gradient method | |
|---|---|---|
| | Buffer A | Buffer B |
| Linear pH concentration gradient (pH 6.0-8.0) | 20 mM NaPi, pH 6.0 | 20 mM NaPi, pH 8.0 |
| Linear salt concentration gradient (NaCl 50-200 mM) | 20 mM Na Acetate, 50 mM NaCl, pH 5.0 | 20 mM Na Acetate, 200 mM NaCl, pH 5.0 |

Figure 6A:
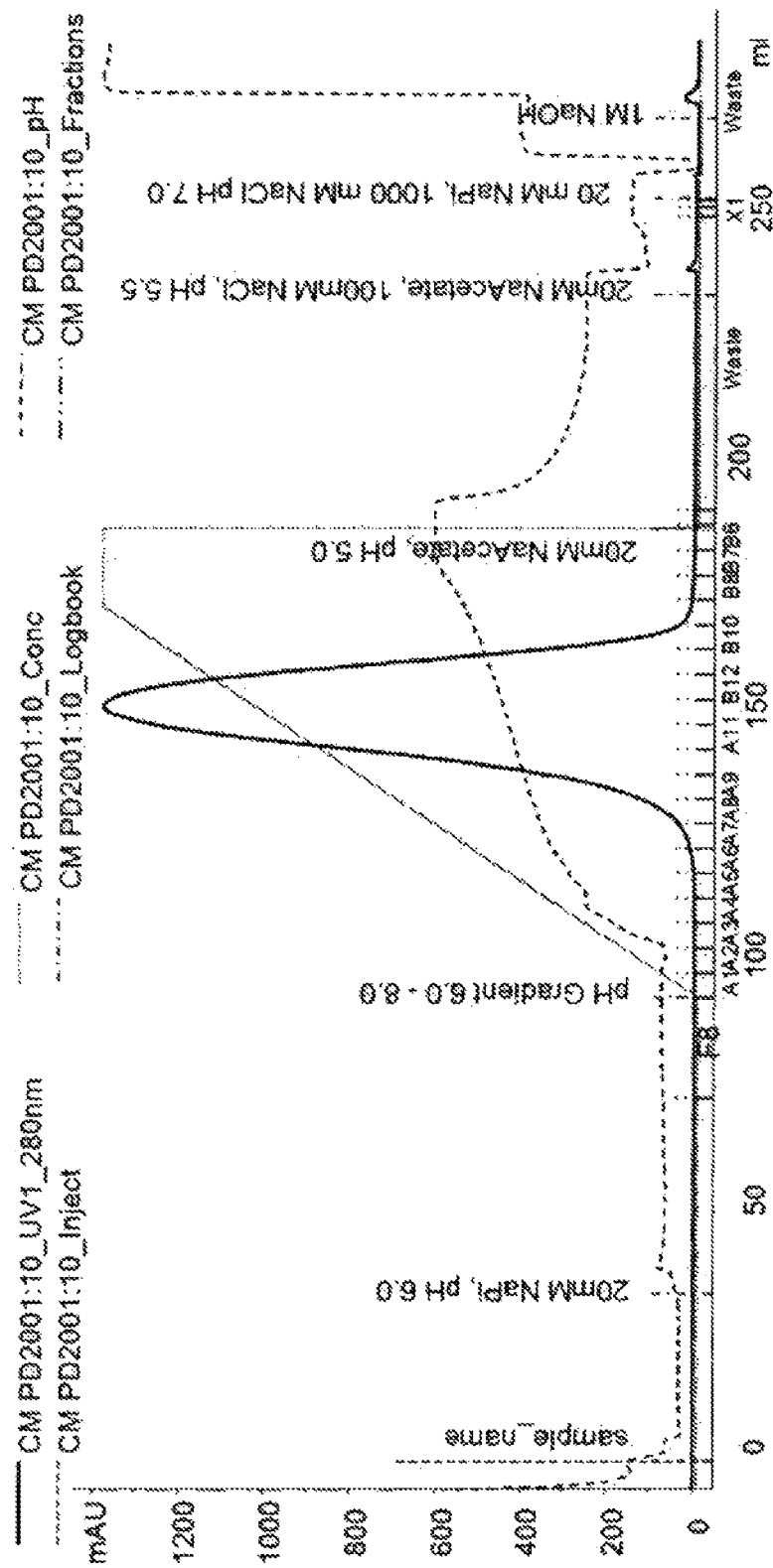
FIGS. 6a and 6b show chromatograms obtained using a linear pH gradient and a linear salt concentration gradient, respectively, according to an embodiment of the present invention.
Figure 6B:
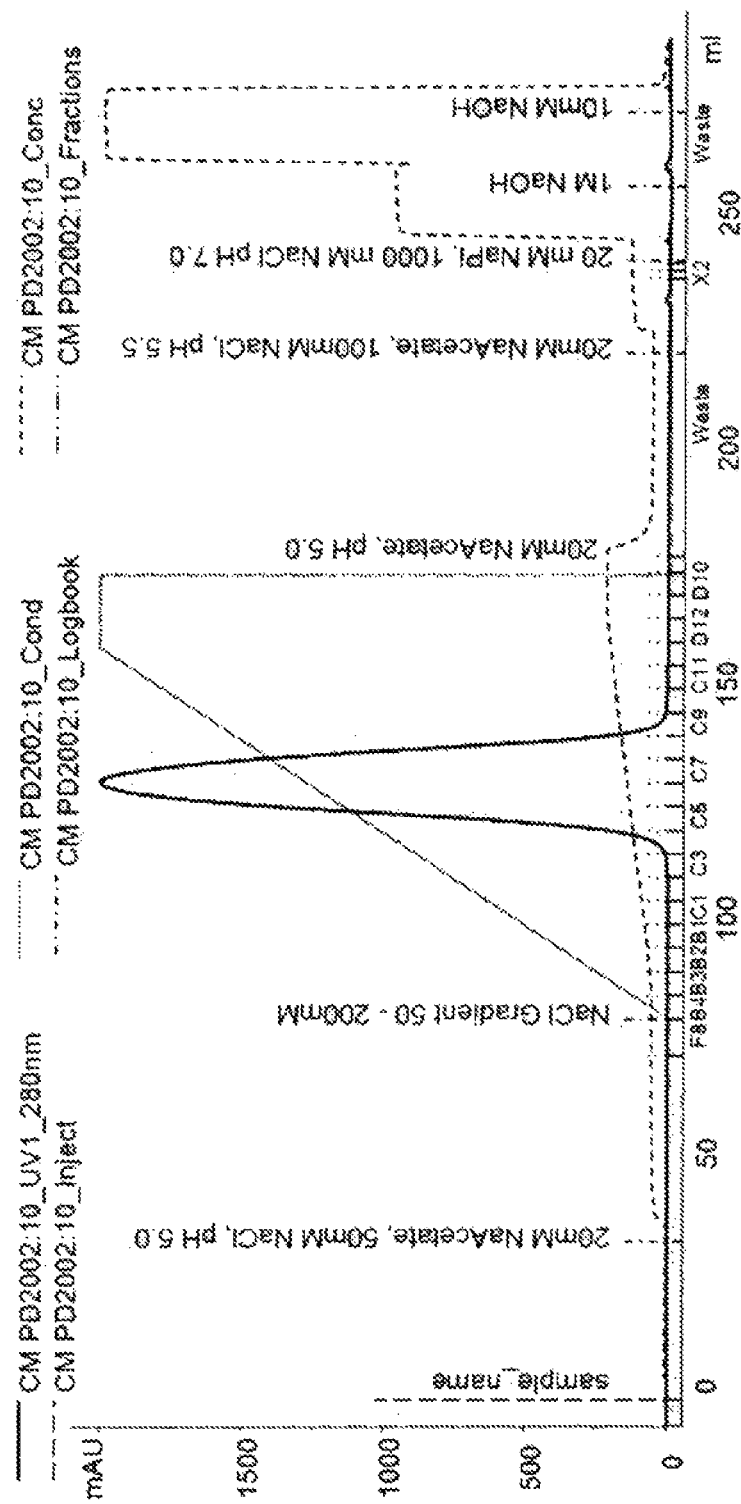

The chromatogram shown in FIG. 6a was produced by the linear pH gradient, and the chromatogram shown in FIG. 6b was produced by the linear salt concentration gradient. Referring to the chromatograms, it can be seen that the UV signal increased in the first elution step while the pH or the salt concentration increased little by little, suggesting that in the case of the proteins eluted early in the chromatogram, isoforms weakly attached to the cation exchange resin were detached.

After the linear pH gradient elution and the linear salt concentration gradient elution, each eluate was collected as a 5 ml fraction. The linear pH gradient eluate was collected as eight eluate fractions (from A8 to B10), and the linear salt concentration gradient eluate was collected as six eluate fractions (from C4 to C9). The glycans in the Fab portion of the antibody included in each eluate fraction were analyzed by intact mass analysis using LC/MS. The results of the analysis are shown in Tables 7 and 8 below.

TABLE 7

Results of analysis of Fab glycans in linear pH concentration gradient eluate fractions

| | 4GlcNAc, 3Hex, F | 4GlcNAc, 4Hex, F | 4GlcNAc, 5Hex, F | 4GlcNAc, 6Hex, F | 4GlcNAc, 7Hex, F | 4GlcNAc, 6Hex, F, NGNA | 5GlcNAc, 7Hex, F |
|---|---|---|---|---|---|---|---|
| Eluate fraction | G0F | G1F | G2F | G2F + 1aGal | G2F + 2aGal | G2F + 1aGal + 1NGNA | — |
| A8 | 0.0 | 0.0 | 0.0 | 1.9 | 7.0 | 25.9 | 2.6 |
| A9 | 0.0 | 0.0 | 0.0 | 2.2 | 6.7 | 26.3 | 2.4 |
| A10 | 0.0 | 0.0 | 0.0 | 2.8 | 7.5 | 30.6 | 2.4 |
| A11 | 0.0 | 0.0 | 0.6 | 3.9 | 12.6 | 34.2 | 2.8 |
| A12 | 0.6 | 1.1 | 2.1 | 5.0 | 20.5 | 30.7 | 2.8 |
| B12 | 4.5 | 3.6 | 4.8 | 5.4 | 27.9 | 23.0 | 2.6 |
| B11 | 10.7 | 6.6 | 7.3 | 5.8 | 30.5 | 14.6 | 2.5 |
| B10 | 17.5 | 9.5 | 9.0 | 5.5 | 30.5 | 8.3 | 2.1 |

| | | 4GlcNAc, 5Hex, F, 2NGNA | 5GlcNAc, 8Hex, F | 5GlcNAc, 9Hex, F | 5GlcNAc, 8Hex, F, NGNA | 5GlcNAc, 7Hex, F, 2NGNA | |
|---|---|---|---|---|---|---|---|
| | Eluate fraction | G2F + 2NGNA | — | — | — | — | Sum |
| | A8 | 25.4 | 4.0 | 4.1 | 15.1 | 14.1 | 100.0 |
| | A9 | 26.7 | 3.5 | 3.8 | 14.7 | 13.7 | 100.0 |
| | A10 | 21.9 | 3.3 | 4.0 | 17.0 | 10.4 | 100.0 |
| | A11 | 13.2 | 2.8 | 6.4 | 17.0 | 6.5 | 100.0 |
| | A12 | 7.1 | 2.6 | 10.1 | 14.3 | 3.0 | 100.0 |
| | B12 | 3.1 | 2.5 | 11.9 | 9.7 | 1.0 | 100.0 |
| | B11 | 1.0 | 2.3 | 12.9 | 5.8 | 0.0 | 100.0 |
| | B10 | 0.0 | 2.2 | 12.1 | 3.3 | 0.0 | 100.0 |

TABLE 8

Results of analysis of Fab glycans in linear salt concentration gradient eluate fractions

| | 4GlcNAc, 3Hex, F | 4GlcNAc, 4Hex, F | 4GlcNAc, 5Hex, F | 4GlcNAc, 6Hex, F | 4GlcNAc, 7Hex, F | 4GlcNAc, 6Hex, F, NGNA | 5GlcNAc, 7Hex, F |
|---|---|---|---|---|---|---|---|
| Eluate fraction | G0F | G1F | G2F | G2F + 1aGal | G2F + 2aGal | G2F + 1aGal + 1NGNA | — |
| C4 | 0.0 | 0.0 | 0.0 | 3.2 | 13.4 | 28.9 | 2.6 |
| C5 | 0.0 | 0.0 | 1.2 | 4.0 | 17.0 | 29.6 | 2.5 |
| C6 | 1.3 | 1.2 | 2.2 | 4.5 | 19.7 | 28.3 | 2.8 |
| C7 | 3.5 | 2.4 | 3.6 | 4.7 | 21.8 | 26.1 | 2.6 |
| C8 | 6.1 | 4.3 | 4.7 | 5.3 | 23.8 | 22.8 | 2.5 |
| C9 | 7.7 | 5.0 | 4.9 | 5.4 | 24.8 | 21.0 | 2.6 |

| | | 4GlcNAc, 5Hex, F, 2NGNA | 5GlcNAc, 8Hex, F | 5GlcNAc, 9Hex, F | 5GlcNAc, 8Hex, F, NGNA | 5GlcNAc, 7Hex, F, 2NGNA | |
|---|---|---|---|---|---|---|---|
| | Eluate fraction | G2F + 2NGNA | — | — | — | — | Sum |

TABLE 8-continued

Results of analysis of Fab glycans in linear salt concentration gradient eluate fractions

| | | | | | | |
|---|---|---|---|---|---|---|
| C4 | 15.3 | 2.9 | 6.7 | 18.0 | 9.1 | 100.00 |
| C5 | 12.5 | 2.9 | 8.2 | 15.7 | 6.4 | 100.00 |
| C6 | 9.9 | 2.5 | 9.6 | 13.3 | 4.7 | 100.00 |
| C7 | 7.9 | 2.3 | 10.0 | 11.7 | 3.4 | 100.00 |
| C8 | 5.7 | 2.5 | 10.5 | 9.7 | 2.0 | 100.00 |
| C9 | 4.8 | 2.3 | 10.4 | 9.3 | 1.8 | 100.00 |

Like the case of Example 2-1, it can be seen that the cause by which isoforms having different charges were produced is a portion including NGNA (N-glycolylneuraminic acid) in the glycans of the antibody Fab. In addition, as can be seen in Tables 7 and 8 above, the levels of NGNA in the early eluted fractions among the linear concentration gradient eluate fractions were higher. This suggests that the linear pH gradient and the linear salt concentration gradient have similar tendencies and that the antibody isoforms which are desired to be separated can be separated by these methods.

Example 3

Separation of Anti-CD20 Monoclonal Antibody Isoforms by Cation Exchange Chromatography An adjusted protein A eluate was prepared by the method as described in Example 1. The adjusted protein A eluate was loaded onto cation exchange chromatography resin (CM Sepharose Fast Flow, GE Healthcare) to thereby separate isoforms of anti-CD20 monoclonal antibody (pI: 9.4-9.6).
*Chromatography Conditions:
Resin: CM Sepharose Fast Flow
Flow rate: 300 cm/h
Equilibration: 50 mM Na Acetate, pH 5.0 buffer
Loading: 7.5 g of protein/L of resin volume
Sterilization: 1 M NaOH solution
Regeneration: 20 mM Na Phosphate, 1000 mM NaCl, pH 5.5 buffer
Washing: 50 mM Na Acetate, 43 mM NaCl, pH 6.0 and pH 6.1 buffer
Elution: 50 mM NaPi, 50 mM NaCl, pH 7.4

The experiment was performed according to the procedure shown in FIG. 7. The adjusted protein A eluate was loaded onto a cation exchange chromatography column, and the monoclonal antibody bound to the column was equilibrated with 6 column volumes of equilibration buffer, and then washed with 10 column volumes of washing buffer, followed by equilibration with 6 column volumes of equilibration buffer. For elution, the product started to be collected when the UV signal increased to 40 mAU, and the product collection was completed when the UV signal decreased by 40 mAU. Herein, as the washing buffer, two kinds of washing buffer having the same composition, but having different pHs, were used for comparison of the results. Isoforms in the resulting eluates were analyzed by CEX-HPLC.

TABLE 9

Results of yield caused by washing and CEX-HPLC analysis

| | | Area of peak (%) | | | | | | | | | | |
|---|---|---|---|---|---|---|---|---|---|---|---|---|
| Sample | Yield (%) | PEAK 1 | PEAK 2 | PEAK 3 | PEAK 4 | PEAK 5 | PEAK 6 | PEAK 7 | PEAK 8 | Acidic peaks | Main peaks | Basic peaks |
| Loaded solution | N/A | 8.38 | 5.76 | 68.58 | 8.08 | 5.58 | 1.78 | 1.45 | 0.41 | 14.14 | 68.58 | 17.3 |
| Eluate 1 | 83.22 | 5.86 | 5.86 | 71.56 | 9.29 | 4.33 | 1.74 | 0.99 | 0.37 | 11.72 | 71.56 | 16.72 |
| Eluate 2 | 67.10 | 3.84 | 4.76 | 72.12 | 9.65 | 5.95 | 2.11 | 1.17 | 0.41 | 8.6 | 72.12 | 19.29 |

Acidic peaks=Peak 1+2, Basic peaks=Peak 4+5+6+7+8

Each of the eluates was analyzed (Table 9), and as a result, it was shown that eluate 2 obtained by elution after washing with the pH 6.1 buffer contained acidic isoforms in smaller amounts than eluate 1 obtained by elution after washing with the pH 6.0 buffer having the same composition as that of the pH 6.1 buffer, and eluate 1 also contained acidic isoforms in smaller amounts than the loaded protein solution.

Figure 8A:
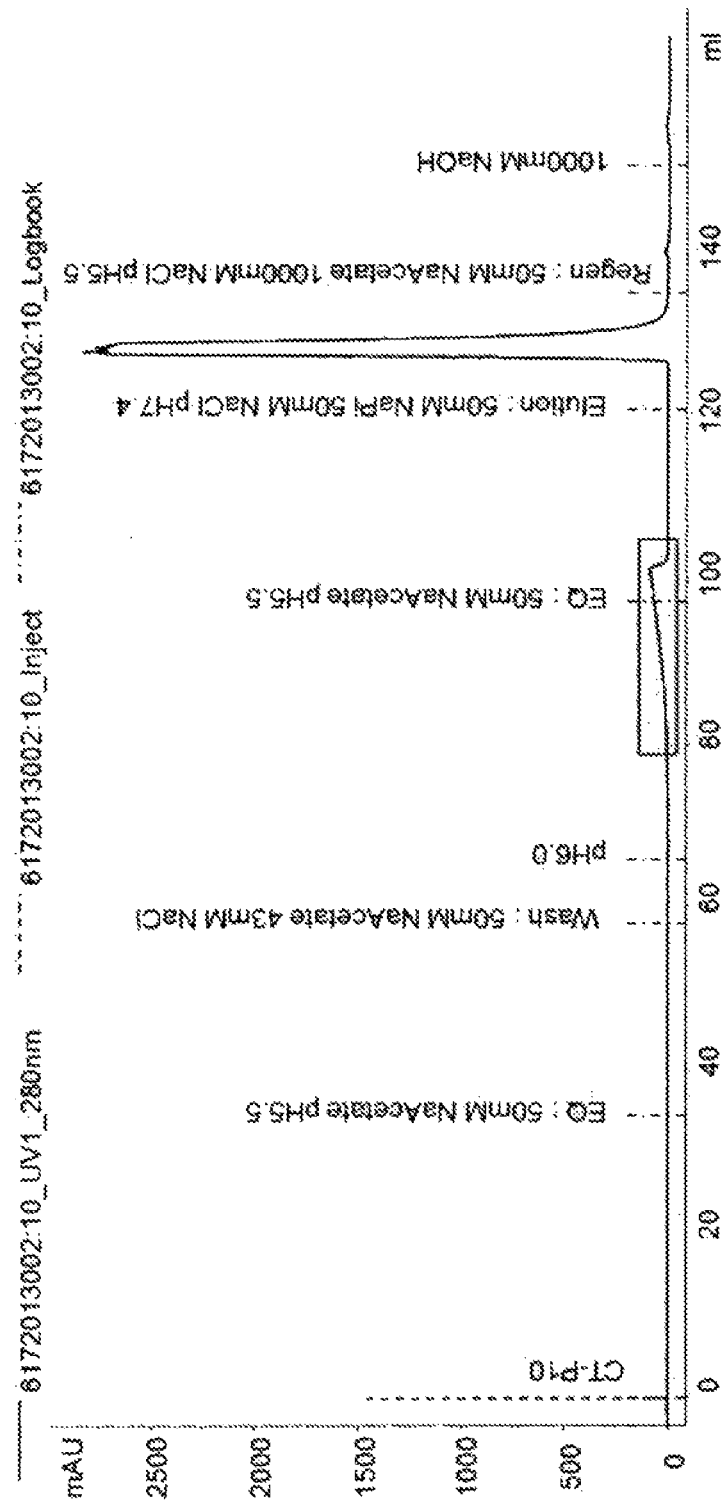
FIGS. 8a and 8b show chromatograms obtained using a washing buffer (50 mM Na acetate, 43 mM NaCl, pH 6.0) and a washing buffer (50 mM Na acetate, 43 mM NaCl, pH 6.1), respectively, according to an embodiment of the present invention.
Figure 8B:
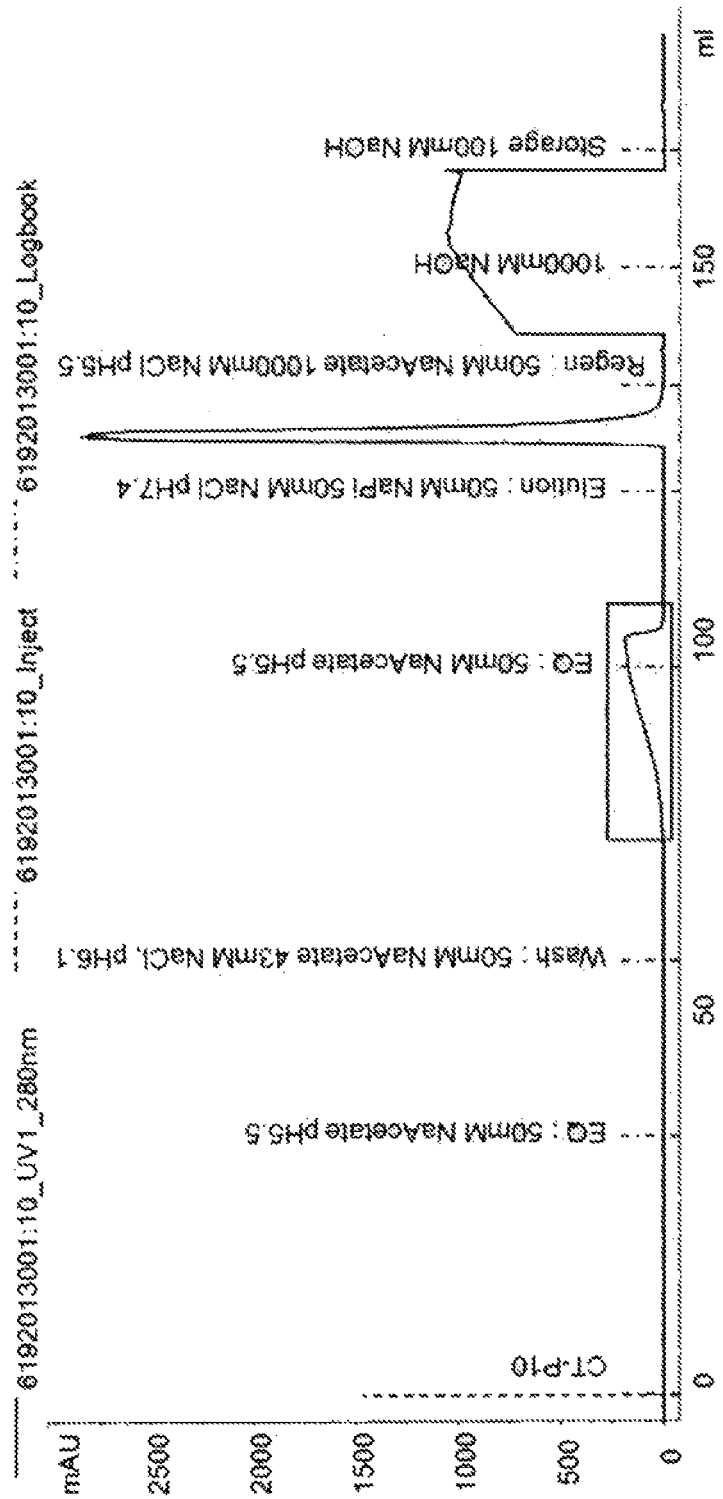

From FIGS. 8a and 8b, it can be seen that the UV signal increased in the washing process, suggesting that acidic isoforms were separated and detached from the column in this process, and the yield was also reduced due to this detachment.

The invention claimed is:

1. A method for separating acidic isoforms of an antibody, comprising the steps of:
   a) loading a sample containing an antibody and acidic isoforms of the antibody onto a cation exchange chromatography column equilibrated with an equilibration buffer having a pH of 5.0-5.5;
   b) loading a washing buffer having a pH of 6.0-8.0 which is at least 1.0 lower than a pI of the antibody onto the cation exchange chromatography column and washing the column by single-step gradient method so that the acidic isoforms of the antibody are separated from the column, the washing buffer having a salt concentration of 10-300 mM; and
   c) recovering a target antibody from the column using an elution buffer having a pH of 5.5-7.4;
   wherein the sample containing an antibody and acidic isoforms of the antibody loaded onto the equilibrated cation exchange chromatography column in step a) is an eluate of protein A affinity chromatography; and
   wherein the washing buffer of step b) is a mixture of a buffer having a pH of 6.0 and a buffer having a pH of 8.0 mixed at a ratio of about 70:30 to about 60:40.

2. The method of claim 1, wherein a conductivity of the washing buffer in step b) is 0.5-50 mS/cm.

3. The method of claim 1, wherein the antibody-containing sample in step a) is adjusted to a conductivity between 0.1 mS/cm and 10 mS/cm before loading.

4. The method of claim 1, further comprising, before step a) or after step c), a step of purifying the antibody-containing sample by loading the antibody-containing sample onto any one chromatography column selected from the group consisting of an ion exchange chromatography column, a hydrophobic interaction chromatography column and a mixed-mode chromatography column.

5. The method of claim 1, wherein the washing buffer is any one selected from the group consisting of sodium citrate, sodium acetate, sodium chloride, sodium phosphate, sodium sulfate, potassium chloride, potassium sulfate, potassium phosphate, Tris, MES (2-(N-morpholino)ethanesulfonic acid), HEPES (4-(2-hydroxyethyl)-1-piperazineethanesulfonic acid), and CHAPS (3-[(3-cholamidopropyl)-dimethylammonio]-1-propane sulfonate).

6. A method for producing an antibody preparation, comprising a purification process that uses the method of claim 1.

* * * * *